(12) United States Patent
Rieping (10) Patent No.: US 7,638,313 B2
(45) Date of Patent: Dec. 29, 2009

(54) **PROCESSES FOR THE FERMENTATIVE PREPARATION OF L-THREONINE USING STRAINS OF *ESCHERICHIA* IN WHICH THE YJGF GENE IS INACTIVATED**

(75) Inventor: Mechthild Rieping, Bielefeld (DE)

(73) Assignee: Degussa AG, Dusseldorf (DE)

( * ) Notice: Subject to any disclaimer, the term of this patent is extended or adjusted under 35 U.S.C. 154(b) by 972 days.

(21) Appl. No.: 10/733,776

(22) Filed: Dec. 12, 2003

(65) Prior Publication Data
US 2004/0191885 A1    Sep. 30, 2004

(30) Foreign Application Priority Data
Jan. 30, 2003    (DE) ................ 103 03 571

(51) Int. Cl.
*C12P 13/08*    (2006.01)
(52) U.S. Cl. ..................................... 435/115
(58) Field of Classification Search ........................ None
See application file for complete search history.

(56) References Cited

U.S. PATENT DOCUMENTS

| 4,278,765 A | 7/1981 | Debabov et al. ............ 435/172 |
| 2007/0092950 A1 * | 4/2007 | Kruse et al. ................. 435/106 |

FOREIGN PATENT DOCUMENTS

| DE | 101 32 946 A1 | 7/2001 |
| DE | 101 35 053 A1 | 7/2001 |
| EP | 0 271 838 A2 | 6/1988 |
| EP | 0 994 190 A2 | 4/2000 |
| EP | 1 013 765 A1 | 6/2000 |
| EP | 1 149 911 A2 | 10/2001 |
| WO | WO 99/18228 | 4/1999 |
| WO | WO 99/53035 | 10/1999 |
| WO | WO 01/05939 A1 | 1/2001 |
| WO | WO 01/92545 A1 | 12/2001 |
| WO | WO 02/06459 A1 | 1/2002 |
| WO | WO 02/29080 A2 | 4/2002 |
| WO | WO 02/36797 A2 | 5/2002 |
| WO | WO 02/064808 A1 | 8/2002 |
| WO | WO 02/077183 | 10/2002 |
| WO | WO 02/081698 A2 | 10/2002 |
| WO | WO 02/081721 A2 | 10/2002 |
| WO | WO 02/081722 A2 | 10/2002 |
| WO | WO 03/004598 A2 | 1/2003 |
| WO | WO 03/004663 A2 | 1/2003 |
| WO | WO 03/004664 A2 | 1/2003 |
| WO | WO 03/004665 A2 | 1/2003 |
| WO | WO 03/004669 A2 | 1/2003 |
| WO | WO 03/004670 A2 | 1/2003 |
| WO | WO 03/004671 A2 | 1/2003 |
| WO | WO 03/004674 A2 | 1/2003 |
| WO | WO 03/006666 A2 | 1/2003 |
| WO | WO 03/008603 A2 | 1/2003 |
| WO | WO 03/008604 A2 | 1/2003 |
| WO | WO 03/008605 A2 | 1/2003 |
| WO | WO 03/008606 A2 | 1/2003 |
| WO | WO 03/008607 A2 | 1/2003 |
| WO | WO 03/008608 A2 | 1/2003 |
| WO | WO 03/008609 A2 | 1/2003 |
| WO | WO 03/008610 A2 | 1/2003 |
| WO | WO 03/008612 A2 | 1/2003 |
| WO | WO 03/008613 A2 | 1/2003 |
| WO | WO 03/008614 A2 | 1/2003 |
| WO | WO 03/008615 A2 | 1/2003 |
| WO | WO 03/038106 A2 | 5/2003 |
| WO | WO 03/076635 A1 | 9/2003 |
| WO | WO 03/076637 | 9/2003 |
| WO | 2005/014841 * | 2/2005 |

OTHER PUBLICATIONS

Lehninger et a., Principles of Biochemistry, 1997, Worth Publishers, 2nd Edition, pp. 697-715.*
Stedman's Online Medical Dictionary (www.stedmans.com) definition of the term "analysis," last viewed on Dec. 11, 2006.*
Spackman et al., Analytical Chemistry 30: 1190-1206, 1958.*
Verkhovskaya et al., Microbiol. 147:3005-3013, 2001.*
Promega Technical Bulletin No. 117 (Sep. 2002).*
Kruse et al., Appl. Microbiol. Biotechnol. 59:205-210, 2002.*
Lee, "High cell-density culture of *Escherichia coli*", Trends Biotechnol. 14:98-105, 1996.*
Voet et al., "Biochemistry, 2nd Edition", John Wiley and Sons, Inc., New York, 1995, pp. 770-773.*
Andrews, et al., "Cloning, Sequencing, and Mapping of the Bacterioferritin Gene (*bfr*) of *Escherichia coli* K-12," *J. Bacteriol.* 171:3940-3947 (1989).
Blankenhorn, et al., "Acid- and Base-Induced Proteins during Aerobic and Anaerobic Growth of *Escherichia coli* Revealed by Two-Dimensional Gel Electrophoresis," *J. Bacteriol.* 181:2209-2216 (1999).
Blattner, et al., "The Complete Genome Sequence of *Escherichia coli* K-12," *Science* 277:1453-1462 (1997).
Boos, et al., "Maltose/Maltodextrin System of *Escherichia coli*: Transport, Metabolism, and Regulation," *Microbiol. Mol. Biol. Rev.* 62:204-229 (1998).
Brune, et al., "Cloning and Sequencing of the Adenylate Kinase Gene (*adk*) of *Escherichia coli*," *Nucleic Acids Res.* 13:7139-7151 (1985).
Carrier, et al., "Library of Synthetic 5' Secondary Structures to Manipulate mRNA Stability in *Escherichia coli*," *Biotechnol. Prog.* 15:58-64 (1999).
Clarke, et al., "Nucleotide Sequence of the *pntA* and *pntB* Genes Encoding the Pyridine-Nucleotide Transhydrogenase of *Escherichia coli*," *Eur. J. Biochem.* 158:647-653 (1986).

(Continued)

Primary Examiner—David J Steadman
(74) Attorney, Agent, or Firm—Law Office of: Michael A. Sanzo, LLC (57) ABSTRACT

The invention relates to a process for the preparation of L-amino acids, in particular L-threonine, in which the following steps are carried out: a) fermentation of microorganisms of the Enterobacteriaceae family which produce the desired L-amino acid and in which the yjgF ORF or the nucleotide sequence which codes for it are attenuated, in particular eliminated, b) concentration of the L-amino acid in the medium or in the cells of the bacteria, and optionally c) isolation of the L-amino acid.

13 Claims, 1 Drawing Sheet

OTHER PUBLICATIONS

Cole, et al., "The Nucleotide Sequence of the *malT* Gene Encoding the Positive Regulator of *Escherichia coli* Maltose Regulon," *Gene* 42:201-208 (1986).

Danot, "A Complex Signaling Module Governs the Activity of MalT, the Prototype of an Emerging Transactivator Family," *Proc. Natl. Acad. Sci. USA* 98:435-440 (2001).

DiRusso, "Nucleotide Sequence of the *fadR* Gene, a Multifunctional Regulator of Fatty Acid Metabolism in *Escherichia coli*," *Nucleic Acids Res.* 16:7995-8009 (1988).

Enos-Berlage, et al., "Complex Metabolic Phenotypes Caused by a Mutation in *yigF*, Encoding a Member of the Highly Conserved YER057c/YjgF Family of Proteins," *J. Bacteriol.* 180:6519-6528 (1998).

Fountoulakis, et al., "Enrichment of Low Abundance Proteins of *Escherichia coli* by Hydroxyapatite Chromatography," *Electrophoresis* 20:2181-2195 (1999).

Franch, et al., "U-Turns and Regulatory RNAs," *Curr. Opin. Microbiol.* 3:159-164 (2000).

Garrido-Pertierra, "Isolation and Properties of *Salmonella typhimurium* Mutants Defective in Enolase," *Revista Española de Fisiologia* 36:33-40 (1980).

Gulick, et al., "Evolution of Enzymatic Activities in the Enolase Superfamily: Crystal Structures of the L-Ala-D/L-Glu Epimerases from *Escherichia coli* and *Bacillus subtilis*," *Biochemistry* 40:15716-15724 (2001).

Heim, et al., "Cloning an *Escherichia coli* Gene Encoding a Protein Remarkably Similar to Mammalian Aldehyde Dehydrogenases," *Gene* 99:15-23 (1991).

Hofnung, Divergent Operons and the Genetic Structure of the Maltose B Region in *Escherichia coli* K12, *Genetics* 76:169-184 (1974).

Hogg, et al., "Nucleotide Sequence and Analysis of the *mgl* Operon of *Escherichia coli* K12," *Mol. Gen. Genet.* 229:453-459 (1991).

Jensen, et al., "Artificial Promoters for Metabolic Optimization," *Biotechnol. Bioeng.* 58:191-195 (1998).

Kaga, et al., "Rnase G-Dependent Degradation of the *eno* mRNA Encoding a Clycolysis Enzyme Enolase in *Escherichia coli*," *Biosci. Biotechnol. Biochem.* 66:2216-2220 (2002).

Kirkpatrick, et al., "Acetate and Formate Stress: Opposite Responses in the Proteome of *Escherichia coli*," *J. Bacteriol.* 183:6466-6477 (2001).

Klein, et al., "Cloning, Nucleotide Sequence, and Functional Expression of the *Escherichia coli* Enolase (*eno*) Gene in a Temperature-Sensitive *eno* Mutant Strain," *J. Seq. Mapping* 6:351-355 (1996).

Knappe, et al., "A Radical-Chemical Route to Acetyl-CoA: The Anaerobically Induced Pyruvate Formate-Lyase System of *Escherichia coli*," *FEMS Microbiol. Rev.* 75:383-398 (1990).

Komatsubara, et al., "Transductional Construction of a Threonine-Producing Strain of *Serratia marcescens*," *Appl. Environ. Microbiol.* 38:1045-1051 (1979).

Landgraf, et al., "The Role of H-NS in One Carbon Metabolism," *Biochimie* 76:1063-1070 (1994).

Lee, et al., "Global Analysis of Transcriptomes and Proteomes of a Parent Strain and an L-Threonine-Overproducing Mutant Strain," *J. Bacteriol.* 185:5442-5451 (2003).

MacPherson, et al., "Identification of the GalP Galactose Transport Protein of *Escherichia coli*," *J. Biol. Chem.* 258:4390-4396 (1983).

Martin, et al., "Forskolin Specifically Inhibits the Bacterial Galactose-H$^+$ Transport Protein, GalP,"*J. Biol. Chem.* 269:24870-24877 (1994).

Masuda, et al., "Improvement of Nitrogen Supply for L-Threonine Production by a Recombinant Strain of *Serratia marcescens*," *Appl. Biochem. Biotechnol.* 37:255-265 (1992).

McPherson, et al., "Complete Nucleotide Sequence of the *Escherichia coli gdhA* Gene," *Nucleic Acids Res.* 11:5257-5267 (1983).

Meyer, et al., Molecular Characterization of Glucokinase from *Escherichia coli* K-12, *J. Bacteriol.* 179:1298-1306 (1997).

Missiakas, et al., "Modulation of the *Escherichia coli* σ$^E$ (RpoE) Heat-Shock Transcription-Factor Activity by the RseA, RseB and RseC Proteins," *Mol. Microbiol.* 24:355-371 (1997).

Nagelkerke, et al., "2-Deoxygalactose, a Specific Substrate of the *Salmonella typhimurium* Galactose Permease: Its Use for the Isolation of *galP* Mutants," *J. Bacteriol.* 133:607-613 (1978).

Niersbach, et al., "Cloning and Nucleotide Sequence of the *Escherichia coli* K-12 *ppsA* Gene, Encoding PEP Synthase," *Mol. Gen. Genet.* 231:332-336 (1992).

Parsons, et al., "Solution Structure and Functional Ligand Screening of HI0719, a Highly Conserved Protein from Bacteria to Humans in the YjgF/YER057c/UK114 Family," *Biochemistry* 42:80-89 (2003).

Postma, "Galactose Transport in *Salmonella typhimurium*," *J. Bacteriol.* 129:630-639 (1977).

Qiu, et al., "The *Escherichia coli polB* Locus Is Identical to *dinA*, the Structural Gene for DNA Polymerase II," *J. Biol. Chem.* 272:8611-8617 (1997).

Raibaud, et al., "Maltotriose Is the Inducer of the Maltose Regulon of *Escherichia coli*," *J. Bacteriol.* 169:3059-3061 (1987).

Raibaud, et al., "Essential and Nonessential Sequences in *malPp*, a Positively Controlled Promoter in *Escherichia coli*," *J. Bacteriol.* 161:1201-1208 (1985).

Ravnikar, et al., "Structural and Functional Analysis of a Cloned Segment of *Escherichia coli* DNA That Specifies Proteins of a $C_4$ Pathway of Serine Biosynthesis," *J. Bacteriol.* 169:4716-4721 (1987).

Reyes, et al., "Overproduction of MalK Protein Prevents Expression of the *Escherichia coli mal* Regulon," *J. Bacteriol.* 170:4598-4602 (1988).

Richet, et al., "MalT, the Regulatory Protein of the *Escherichia coli* Maltose System, Is an ATP-Dependent Transcriptional Activator," *Embo J.* 8:981-987 (1989).

Rödel, et al., "Primary Structures of *Escherichia coli* Pyruvate Formate-Lyase and Pyruvate-Formatre-Lyase-Activating Enzyme Deduced from the DNA Nucleotide Sequences," *Eur. J. Biochem.* 177:153-158 (1988).

Romeo, et al., "Identification and Molecular Characterizatrion of *csrA*, a Pleiotropic Gene from *Escherichia coli* That Affects Glycogen Biosynthesis, Gluconeogenesis, Cell Size, and Surface Properties," *J. Bacteriol.* 175:4744-4755 (1993).

Sabe, et al., "Molecular Cloning of the Phosphoenolpyruvate Carboxylase Gene, *ppc*, of *Escherichia coli*," *Gene* 31:279-283 (1984).

Schlegel, et al., "Network Regulation of the *Escherichia coli* Maltose System," *J. Mol. Microbiol. Biotechnol.* 4:301-307 (2002).

Schmitz, et al., "Reduced Transaminase B (IlvE) Activity Caused by the Lack of *yjgF* Is Dependent on the Status of Threonine Deaminase (IlvA) in *Salmonella enterica* Serovar Typhimurium," *J. Bacteriol.* 186:803-810 (2004).

Schreiber, et al., "A New Mechanism for the Control of Prokaryotic Transcriptional Regulator: Antagonistic Binding of Positive and Negative Effectors," *Mol. Microbiol.* 35:765-776 (2000).

Spring, et al., "The Purification and Characterization of *Escherichia coli* Enolase," *J. Biol. Chem.* 246:6797-6802 (1971).

Stephens, et al., "The Pyruvate Dehydrogenase Complex of *Escherichia coli* K12—Nucleotide Sequence Encoding the Pyruvate Dehydrogenase Component," *Eur. J. Biochem.* 133:155-162 (1983).

Stephens, et al., "The Pyruvate Dehydrogenase Complex of *Escherichia coli* K12—Nucleotide Sequence Encoding the Dihydrolipoamide Acetyltransferase Component," *Eur. J. Biochem.* 133:481-489 (1983).

Stephens, et al., "Nucleotide Sequence of the Lipoamide Dehydrogenase Gene of *Escherichia coli* K12," *Eur. J. Biochem.* 135:519-527 (1983).

Sugita, et al., "Cloning and Characterization of the Mutated Threonine Operon ($thrA_1 5A_2 5BC$) of *Serratia marcescens*," *Gene* 57:151-158 (1987).

Sunnarborg, et al., "Regulation of the Glyoxylate Bypass Operon: Cloning and Characterization of *iclR*," *J. Bacteriol.* 172:2642-2649 (1990).

Suzuki, et al., "Mapping, Cloning, and DNA Sequencing of *pepB* Which Encodes Peptidase B of *Escherichia coli* K-12," *J. Ferment. Bioeng.* 82:392-397 (1996).

Thorsness, et al., "Inactivation of Isocitrate Dehydrogenase by Phosphorylation Is Mediated by the Negative Charge of the Phosphate," *J. Biol. Chem.* 262:10422-10425 (1987).

Valle, et al., "Nucleotide Sequence of the Promoter and Amino-Terminal Coding Region of the Glutamate Dehydrogenase Structural Gene of *Escherichia coli*," *Gene 23*:199-209 (1983).

Venter, et al., "Molecular Dissection of Membrane-Transport Proteins: Mass Spectrometry and Sequence Determination of the Galactose-$H^+$ Symport Protein, GalP, of *Escherichia coli* and Quantitative Assay of the Incorporation of [*ring*-$2^{13}$C]histidine and $^{15}NH_3$," *Biochem J. 363*243-252 (2002).

Vidal-Ingigliardi, et al., "A Small C-Terminal Region of the *Escherichia coli* MalT Protein Contains the DNA-Binding Domain," *J. Biol. Chem. 268*:24527-24530 (1993).

Vogel, et al., "Cloning and Sequenc of the *mdh* Structural Gene of *Escherichia coli* Coding for Malate Dehydrogenase," *Arch. Microbiol. 149*:36-42 (1987).

Volz, "A Test Case for Structure-Based Functional Assignment: The 1.2 Å Crystal Structure of the yjgF Gene Product from *Escherichia coli*," *Protein Science 8*:2428-2437 (1999).

Wagner, et al., "The Free Radical in Pyruvate Formate-Lyase Is Located on Glycine-734," *Proc. Natl. Acad. Sci. USA 89*:996-1000 (1992).

Walmsley, et al., "8-Anilino-1-Naphthalenesulfonate Is a Fluorescent Probe of Conformational Changes in the D-Galactose-$H^+$ Simport Protein of *Escherichia coli*," *J. Biol. Chem.269*:17009-17019 (1994).

Walton, et al., "Nucleotide Sequence of the *Escherichia coli* Uridine Phosphorylase (*udp*) Gene," *Nucleic Acids Res. 17*:6741 (1989).

Wasinger, et al., "Small Genes/Gene-Products in *Escherichia coli* K-12," *FEMS Microbiol. Lett. 169*:375-382 (1998).

Wente, et al., "Different Amino Acid Substitutions at the Same Position in the Nucleotide-Binding Site of Aspartate Transcarbamoylase Have Diverse Effects on the Allosteric Properties of the Enzyme," *J. Biol. Chem. 266*:20833-20839 (1991).

Wong, et al., "Transcription of *pfl* Is Regulatred by Anaerobiosis, Catabolite Repression, Pyruvate, and *oxrA: pfl*::MU dA Operon Fusions of *Salmonella typhimurium*," *J. Bacteriol. 171*:4900-4905 (1989).

Wyborn, et al., "Expression of the *Escherichia coli yfiD* Gene Responds to Intracellular pH and Reduces the Accumulation of Acidic Metabolic End Products," *Microbiology 148*:1015-1026 (2002).

Yano, et al., "Directed Evolution of an Aspartate Aminotransferase with New Substrate Specificities," *Proc. Natl. Acad. Sci. USA 95*:5511-5515 (1998).

Yoshida, et al., "Physical Map Location of a Set of *Escherichia coli* Genes (*hde*) Whose Expression Is Affected by the Nucleoid Protein H-NS," *J. Bacteriol. 175*:7747-7748 (1993).

Hermann, et al., "Improved L-Threonine Production with *Escherichia coli*," *Proceedings of European Congress Biotechnology*, XX, XX, Aug. 24, 2003, p. 85.

McClelland, et al., "Complete Genome Sequence of *Salmonella enterica* Serovar Typhimurium LT2," *Nature 413*:852-856 (2001).

Sofia, et al., "Analysis of the *Escherichia coil* Genome. V. DNA Sequence of the Region from 76.0 to 81.5 Minutes," *Nucleic Acids Res. 22*(13):2576-2586 (1994).

Database UniProt 'Online!', Jul. 1, 1898, "Putative Glycosyl Transferase yibD (EC 2.-.-.-)," Accession No. P11290.

Database EMBL 'Online!', Jun. 2, 1994, "*E. coli* Chromosomal Region from 76.0 to 81.5 Minutes," Accession No. V00039.

Database EMBL 'Online!', Oct. 29, 2001, "*Salmonella tphyimurium* LT2, Section 176 of 220 of the Complete Genome," Accession No. AE 008872.

\* cited by examiner

Figure 1: Map of the plasmid pMAK705deltayjgF

SEQUENCE LISTING

```
<160> NUMBER OF SEQ ID NOS: 12

<210> SEQ ID NO 1
<211> LENGTH: 1548
<212> TYPE: DNA
<213> ORGANISM: Escherichia coli
<220> FEATURE:
<221> NAME/KEY: DNA
<222> LOCATION: (1)..(1548)
<223> OTHER INFORMATION:
<220> FEATURE:
<221> NAME/KEY: CDS
<222> LOCATION: (527)..(952)
<223> OTHER INFORMATION: yjgF-Orf

<400> SEQUENCE: 1
tcgcgatctg gtactgtaag gggaaataga gatgacacac gataataaat tgcaggttga     60
agctattaaa cgcggcacgg taattgacca tatcccgcc cagatcggtt ttaagctgtt     120
gagtctgttc aagctgaccg aaacggatca gcgcatcacc attggtctga acctgccttc    180
tggcgagatg ggccgcaaag atctgatcaa aatcgaaaat acctttttga gtgaagatca    240
```

```
agtagatcaa ctggcattgt atgcgccgca agccacggtt aaccgtatcg acaactatga      300
agtggtgggt aaatcgcgcc caagtctgcc ggagcgcatc gacaatgtgc tggtctgccc      360
gaacagcaac tgtatcagcc atgccgaacc ggtttcatcc agctttgccg tgcgaaaacg      420
cgccaatgat atcgcgctca aatgcaaata ctgtgaaaaa gagttttccc ataatgtggt      480
gctggccaat taattgcggt tggtaataaa agtctggctc cctata atg agc cag         535
                                                  Met Ser Gln
                                                    1 act ttt tac cgc tgt aat aaa gga gaa atc atg agc aaa act atc gcg        583
Thr Phe Tyr Arg Cys Asn Lys Gly Glu Ile Met Ser Lys Thr Ile Ala
  5                  10                  15 acg gaa aat gca ccg gca gct atc ggt cct tac gta cag ggc gtt gat        631
Thr Glu Asn Ala Pro Ala Ala Ile Gly Pro Tyr Val Gln Gly Val Asp
 20                  25                  30                  35 ctg ggc aat atg atc atc acc tcc ggt cag atc ccg gta aat ccg aaa        679
Leu Gly Asn Met Ile Ile Thr Ser Gly Gln Ile Pro Val Asn Pro Lys
                 40                  45                  50 acg ggc gaa gta ccg gca gac gtc gct gca cag gca cgt cag tcg ctg        727
Thr Gly Glu Val Pro Ala Asp Val Ala Ala Gln Ala Arg Gln Ser Leu
             55                  60                  65 gat aac gta aaa gcg atc gtc gaa gcc gct ggc ctg aaa gtg ggc gac        775
Asp Asn Val Lys Ala Ile Val Glu Ala Ala Gly Leu Lys Val Gly Asp
         70                  75                  80 atc gtt aaa act acc gtg ttt gta aaa gat ctg aac gac ttc gca acc        823
Ile Val Lys Thr Thr Val Phe Val Lys Asp Leu Asn Asp Phe Ala Thr
     85                  90                  95 gta aac gcc act tac gaa gcc ttc ttc acc gaa cac aac gcc acc ttc        871
Val Asn Ala Thr Tyr Glu Ala Phe Phe Thr Glu His Asn Ala Thr Phe
100                 105                 110                 115 ccg gca cgt tct tgc gtt gaa gtt gcc cgt ctg ccg aaa gac gtg aag        919
Pro Ala Arg Ser Cys Val Glu Val Ala Arg Leu Pro Lys Asp Val Lys
                120                 125                 130 att gag atc gaa gcg atc gct gtt cgt cgc taa tcttgatgga atccgggct       972
Ile Glu Ile Glu Ala Ile Ala Val Arg Arg
                135                 140 atcatgcccg gattaagtct gatgacaaac gcaaaatcgc ctgatgcgct acgcttatca     1032
ggcctacgtg attcctgcaa tttattgaat ttgttggccg gataaggcat ttacgccgca     1092
tccggcatga acaaaactca ctttgtctac aatctgaatc ggggctatcg tgcccagttt     1152
attctttatt gccagccgta acgacggcta tagaacccct tcaccaactg ggttaatgtc     1212
atataccctg ccagaatcgc aaccagccac gggaaatagc ttaacggcag cgcctgtaat     1272
tgcagataac tggccagcgg tgaaaacggc aatgcgatcc cgacaatcat cacgatcacg     1332
gtcatgatca ttaacggcca cgatgcacag ctctgaataa acggcacacg gcgggtgcgg     1392
atcatatgca caatcagcgt ttgcgacagt aagcccacca caaaccatcc cgactggaac     1452
agcgtttgcg tttccggcgt gttggcatgg aatacccacc acatcaggca aaacgtcaaa     1512
atatcgaaga tcgagctgat cggtccgaag aagatc                              1548

<210> SEQ ID NO 2
<211> LENGTH: 141
<212> TYPE: PRT
<213> ORGANISM: Escherichia coli
```

-continued

```
<400> SEQUENCE: 2

Met Ser Gln Thr Phe Tyr Arg Cys Asn Lys Gly Glu Ile Met Ser Lys
1               5                   10                  15

Thr Ile Ala Thr Glu Asn Ala Pro Ala Ala Ile Gly Pro Tyr Val Gln
            20                  25                  30

Gly Val Asp Leu Gly Asn Met Ile Ile Thr Ser Gly Gln Ile Pro Val
        35                  40                  45

Asn Pro Lys Thr Gly Glu Val Pro Ala Asp Val Ala Ala Gln Ala Arg
    50                  55                  60

Gln Ser Leu Asp Asn Val Lys Ala Ile Val Glu Ala Ala Gly Leu Lys
65                  70                  75                  80

Val Gly Asp Ile Val Lys Thr Thr Val Phe Val Lys Asp Leu Asn Asp
                85                  90                  95

Phe Ala Thr Val Asn Ala Thr Tyr Glu Ala Phe Phe Thr Glu His Asn
            100                 105                 110

Ala Thr Phe Pro Ala Arg Ser Cys Val Glu Val Ala Arg Leu Pro Lys
        115                 120                 125

Asp Val Lys Ile Glu Ile Glu Ala Ile Ala Val Arg Arg
    130                 135                 140

<210> SEQ ID NO 3
<211> LENGTH: 20
<212> TYPE: DNA
<213> ORGANISM: Escherichia coli
<220> FEATURE:
<221> NAME/KEY: Primer
<222> LOCATION: (1)..(20)
<223> OTHER INFORMATION: yjgF-1

<400> SEQUENCE: 3
tcgcgatctg gtactgtaag                                              20

<210> SEQ ID NO 4
<211> LENGTH: 20
<212> TYPE: DNA
<213> ORGANISM: Escherichia coli
<220> FEATURE:
<221> NAME/KEY: Primer
<222> LOCATION: (1)..(20)
<223> OTHER INFORMATION: yjgF-2

<400> SEQUENCE: 4
ctgtacgtaa ggaccgatag                                              20

<210> SEQ ID NO 5
<211> LENGTH: 20
<212> TYPE: DNA
<213> ORGANISM: Escherichia coli
<220> FEATURE:
<221> NAME/KEY: Primer
<222> LOCATION: (1)..(20)
<223> OTHER INFORMATION: yjgF-3

<400> SEQUENCE: 5
cgctgttcgt cgctaatctt                                              20

<210> SEQ ID NO 6
<211> LENGTH: 20
<212> TYPE: DNA
<213> ORGANISM: Escherichia coli
```

```
<220> FEATURE:
<221> NAME/KEY: Primer
<222> LOCATION: (1)..(20)
<223> OTHER INFORMATION: yjgF-4

<400> SEQUENCE: 6
gatcttcttc ggaccgatca                                                     20

<210> SEQ ID NO 7
<211> LENGTH: 622
<212> TYPE: DNA
<213> ORGANISM: Escherichia coli
<220> FEATURE:
<221> NAME/KEY: prim_transcript
<222> LOCATION: (1)..(622)
<223> OTHER INFORMATION: PCR product yjgF5'

<400> SEQUENCE: 7
tcgcgatctg gtactgtaag gggaaataga gatgacacac gataataaat tgcaggttga         60
agctattaaa cgcggcacgg taattgacca tatccccgcc cagatcggtt ttaagctgtt        120
gagtctgttc aagctgaccg aaacggatca gcgcatcacc attggtctga acctgccttc        180
tggcgagatg ggccgcaaag atctgatcaa aatcgaaaat accttttttga gtgaagatca      240 agtagatcaa ctggcattgt atgcgccgca agccacggtt aaccgtatcg acaactatga        300
agtggtgggt aaatcgcgcc caagtctgcc ggagcgcatc gacaatgtgc tggtctgccc        360
gaacagcaac tgtatcagcc atgccgaacc ggtttcatcc agctttgccg tgcgaaaacg        420
cgccaatgat atcgcgctca atgcaaata ctgtgaaaaa gagttttccc ataatgtggt        480
gctggccaat taattgcggt tggtaataaa agtctggctc cctataatga ccagactttt       540
ttaccgctgt aataaaggag aaatcatgag caaaactatc gcgacggaaa atgcaccggc       600
agctatcggt ccttacgtac ag                                                 622

<210> SEQ ID NO 8
<211> LENGTH: 612
<212> TYPE: DNA
<213> ORGANISM: Escherichia coli
<220> FEATURE:
<221> NAME/KEY: prim_transcript
<222> LOCATION: (1)..(612)
<223> OTHER INFORMATION: PCR product yjgF3'

<400> SEQUENCE: 8
cgctgttcgt cgctaatctt gatggaaatc cgggctatca tgcccggatt aagtctgatg         60
acaaacgcaa aatcgcctga tgcgctacgc ttatcaggcc tacgtgattc ctgcaattta        120
ttgaatttgt tggccggata aggcatttac gccgcatccg gcatgaacaa aactcacttt        180
gtctacaatc tgaatcgggg ctatcgtgcc cagtttattc tttattgcca gccgtaacga       240
cggctataga accctttcac caactgggtt aatgtcatat accctgccag aatcgcaacc       300
agccacggga aatagcttaa cggcagcgcc tgtaattgca gataactggc cagcggtgaa       360
aacggcaatg cgatcccgac aatcatcacg atcacggtca tgatcattaa cggccacgat      420
gcacagctct gaataaacgg cacacggcgg gtgcggatca tatgcacaat cagcgtttgc     480
gacagtaagc ccaccacaaa ccatcccgac tggaacagcg tttgcgtttc ggcgtgttg       540 gcatggaata cccaccacat caggcaaaac gtcaaaatat cgaagatcga gctgatcggt     600
ccgaagaaga tc                                                            612
```

```
<210> SEQ ID NO 9
<211> LENGTH: 1411
<212> TYPE: DNA
<213> ORGANISM: Artificial sequence
<220> FEATURE:
<221> NAME/KEY: misc_feature
<222> LOCATION: (1)..(1411)
<223> OTHER INFORMATION:
<220> FEATURE:
<221> NAME/KEY: misc_feature
<222> LOCATION: (1)..(57)
<223> OTHER INFORMATION: Technical DNA/residues of polylinker sequence
<220> FEATURE:
<221> NAME/KEY: misc_feature
<222> LOCATION: (58)..(671)
<223> OTHER INFORMATION: Part of the upstream region and part of the 5'
      region of the
      yjgF Orf
<220> FEATURE:
<221> NAME/KEY: misc_feature
<222> LOCATION: (672)..(737)
<223> OTHER INFORMATION: Technical DNA/residues of polylinker sequence
<220> FEATURE:
<221> NAME/KEY: misc_feature
<222> LOCATION: (738)..(1359)
<223> OTHER INFORMATION: Part of the 3' region of the yjgF Orf and part
      of the downstream
      region
<220> FEATURE:
<221> NAME/KEY: misc_feature
<222> LOCATION: (1359)..(1411)
<223> OTHER INFORMATION: Technical DNA/residues of polylinker sequence

<400> SEQUENCE: 9
agcttggtac cgagctcgga tccactagta acggccgcca gtgtgctgga attcgccctt      60
gatcttcttc ggaccgatca gctcgatctt cgatattttg acgttttgcc tgatgtggtg     120
ggtattccat gccaacacgc cggaaacgca acgctgttc cagtcgggat ggtttgtggt      180
gggcttactg tcgcaaacgc tgattgtgca tatgatccgc accgccgtg tgccgtttat      240 tcagagctgt gcatcgtggc cgttaatgat catgaccgtg atcgtgatga ttgtcgggat     300
cgcattgccg ttttcaccgc tggccagtta tctgcaatta caggcgctgc cgttaagcta     360
tttcccgtgg ctggttgcga ttctggcagg gtatatgaca ttaacccagt tggtgaaagg     420
gttctatagc cgtcgttacg gctggcaata agaataaac tgggcacgat agccccgatt      480
cagattgtag acaaagtgag ttttgttcat gccggatgcg gcgtaaatgc cttatccggc     540
caacaaattc aataaattgc aggaatcacg taggcctgat aagcgtagcg catcaggcga     600
ttttgcgttt gtcatcagac ttaatccggg catgatagcc cggatttcca tcaagattag     660
cgacgaacag cgaagggcga attctgcaga tctcggatcc actagtaacg gccgccagtg     720
tgctggaatt cgcccttctg tacgtaagga ccgatagctg ccggtgcatt ttccgtcgcg     780
atagttttgc tcatgatttc tcctttatta cagcggtaaa aagtctggct cattataggg     840
agccagactt ttattaccaa ccgcaattaa ttggccagca ccacattatg ggaaaactct     900
ttttcacagt atttgcattt gagcgcgata tcattggcgc gttttcgcac ggcaaagctg     960
gatgaaaccg gttcggcatg gctgatacag ttgctgttcg ggcagaccag cacattgtcg    1020
atgcgctccg gcagacttgg gcgcgattta cccaccactt catagttgtc gatacggtta    1080
accgtggctt gcggcgcata caatgccagt tgatctactt gatcttcact caaaaaggta    1140
ttttcgattt tgatcagatc tttgcggccc atctcgccag aaggcaggtt cagaccaatg    1200
gtgatgcgct gatccgtttc ggtcagcttg aacagactca acagcttaaa accgatctgg    1260
gcggggatat ggtcaattac cgtgccgcgt ttaatagctt caacctgcaa tttattatcg    1320
```

```
tgtgtcatct ctatttcccc ttacagtacc agatcgcgaa agggcgaatt ctgcagatat    1380
ccatcacact ggcggccgct cgagcatgca t                                   1411

<210> SEQ ID NO 10
<211> LENGTH: 177
<212> TYPE: DNA
<213> ORGANISM: Articifial sequence
<220> FEATURE:
<221> NAME/KEY: misc_feature
<222> LOCATION: (1)..(177)
<223> OTHER INFORMATION:
<220> FEATURE:
<221> NAME/KEY: misc_feature
<222> LOCATION: (1)..(3)
<223> OTHER INFORMATION: Start codon of the delta yjgF Orf
<220> FEATURE:
<221> NAME/KEY: misc_feature
<222> LOCATION: (1)..(99)
<223> OTHER INFORMATION: 5' region of the delta yjgF Orfs
<220> FEATURE:
<221> NAME/KEY: misc_feature
<222> LOCATION: (100)..(162)
<223> OTHER INFORMATION: Technical DNA/residues of polylinker sequence
<220> FEATURE:
<221> NAME/KEY: misc_feature
<222> LOCATION: (163)..(174)
<223> OTHER INFORMATION: 3' region of the delta yjgF Orf
<220> FEATURE:
<221> NAME/KEY: misc_feature
<222> LOCATION: (175)..(177)
<223> OTHER INFORMATION: Stop codon of the delta yjgF Orf

<400> SEQUENCE: 10
atgagccaga cttttttaccg ctgtaataaa ggagaaatca tgagcaaaac tatcgcgacg    60
gaaaatgcac cggcagctat cggtccttac gtacagaagg cgaattcca gcacactggc    120 ggccgttact agtggatccg agatctgcag aattcgccct tcgctgttcg tcgctaa      177

<210> SEQ ID NO 11
<211> LENGTH: 387
<212> TYPE: DNA
<213> ORGANISM: Salmonella typhimurium
<220> FEATURE:
<221> NAME/KEY: CDS
<222> LOCATION: (1)..(387)
<223> OTHER INFORMATION: yjgF Orf

<400> SEQUENCE: 11 atg agc aaa act att gcg acg gaa aat gca cca gca gca atc ggc cca    48
Met Ser Lys Thr Ile Ala Thr Glu Asn Ala Pro Ala Ala Ile Gly Pro
 1               5                  10                  15 tac gta cag ggc gtt gac ctg ggt agc atg gta atc act tcc ggt cag    96
Tyr Val Gln Gly Val Asp Leu Gly Ser Met Val Ile Thr Ser Gly Gln
             20                  25                  30 atc ccg gtc gat ccg aaa acc ggt gcc gta gcg gaa gac gta tcc gct   144
Ile Pro Val Asp Pro Lys Thr Gly Ala Val Ala Glu Asp Val Ser Ala
         35                  40                  45 cag gca cgt cag tcg ctg gaa aac gtt aaa gct atc gtg gaa gcc gct   192
Gln Ala Arg Gln Ser Leu Glu Asn Val Lys Ala Ile Val Glu Ala Ala
     50                  55                  60 ggc ctg aaa gta ggc gac att gtg aaa acg acc gta ttc gtg aaa gac   240
Gly Leu Lys Val Gly Asp Ile Val Lys Thr Thr Val Phe Val Lys Asp
 65                  70                  75                  80 ctg aac gat ttc gcg acc gtc aac gcc acc tac gaa gcc ttc ttc acc   288
Leu Asn Asp Phe Ala Thr Val Asn Ala Thr Tyr Glu Ala Phe Phe Thr
                 85                  90                  95
```

```
                                                -continued gag cac aac gcc acc ttc ccg gcg cgt tcc tgc gtg gaa gtt gcc cgt        336
Glu His Asn Ala Thr Phe Pro Ala Arg Ser Cys Val Glu Val Ala Arg
            100                 105                 110 ctg ccg aaa gac gtg aaa att gag att gaa gcg atc gct gtt cgt cgc        384
Leu Pro Lys Asp Val Lys Ile Glu Ile Glu Ala Ile Ala Val Arg Arg
            115                 120                 125 taa                                                                     387

<210> SEQ ID NO 12
<211> LENGTH: 128
<212> TYPE: PRT
<213> ORGANISM: Salmonella typhimurium

<400> SEQUENCE: 12

Met Ser Lys Thr Ile Ala Thr Glu Asn Ala Pro Ala Ala Ile Gly Pro
1               5                   10                  15

Tyr Val Gln Gly Val Asp Leu Gly Ser Met Val Ile Thr Ser Gly Gln
            20                  25                  30

Ile Pro Val Asp Pro Lys Thr Gly Ala Val Ala Glu Asp Val Ser Ala
            35                  40                  45

Gln Ala Arg Gln Ser Leu Glu Asn Val Lys Ala Ile Val Glu Ala Ala
    50                  55                  60

Gly Leu Lys Val Gly Asp Ile Val Lys Thr Thr Val Phe Val Lys Asp
65                  70                  75                  80

Leu Asn Asp Phe Ala Thr Val Asn Ala Thr Tyr Glu Ala Phe Phe Thr
                85                  90                  95

Glu His Asn Ala Thr Phe Pro Ala Arg Ser Cys Val Glu Val Ala Arg
            100                 105                 110

Leu Pro Lys Asp Val Lys Ile Glu Ile Glu Ala Ile Ala Val Arg Arg
            115                 120                 125
```

PROCESSES FOR THE FERMENTATIVE PREPARATION OF L-THREONINE USING STRAINS OF *ESCHERICHIA* IN WHICH THE *YJGF* GENE IS INACTIVATED

CROSS REFERENCE TO RELATED APPLICATIONS

The present application claims priority to German application 103 03 571.0, filed on Jan. 30, 2003, which is incorporated in its entirety herein by reference.

FIELD OF THE INVENTION

This invention relates to a process for the fermentative preparation of L-amino acids, in particular L-threonine, using strains of the Enterobacteriaceae family in which the open reading frame (ORF) with the designation yjgF is attenuated.

PRIOR ART

L-Amino acids, in particular L-threonine, are used in human medicine and in the pharmaceuticals industry, in the foodstuffs industry and very particularly in animal nutrition.

It is known to prepare L-amino acids by fermentation of strains of Enterobacteriaceae, in particular *Escherichia coli* (*E. coli*) and *Serratia marcescens*. Because of their great importance, work is constantly being undertaken to improve the preparation processes. Improvements to the process can relate to fermentation measures, such as e.g. stirring and supply of oxygen, or the composition of the nutrient media, such as e.g. the sugar concentration during the fermentation, or the working up to the product form, by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the threonine analogue α-amino-β-hydroxyvaleric acid (AHV), or are auxotrophic for metabolites of regulatory importance and produce L-amino acid, such as e.g. L-threonine, are obtained in this manner.

Methods of the recombinant DNA technique have also been employed for some years for improving the strain of strains of the Enterobacteriaceae family which produce L-amino acids, by amplifying individual amino acid biosynthesis genes and investigating the effect on the production. Summarizing information on the cell and molecular biology of *Escherichia coli* and Salmonella are to be found in Neidhardt (ed): *Escherichia coli* and Salmonella, Cellular and Molecular Biology, 2nd edition, ASM Press, Washington, D.C., USA.

OBJECT OF THE INVENTION

The object of the invention is to provide new measures for improved fermentative preparation of L-amino acids, in particular L-threonine.

SUMMARY OF THE INVENTION

The invention provides a process for the fermentative preparation of L-amino acids, in particular L-threonine, using microorganisms of the Enterobacteriaceae family which, in particular, already produce L-amino acids and in which at least the nucleotide sequence which codes for the yjgF ORF or alleles thereof is or are attenuated.

BRIEF DESCRIPTION OF THE FIGURES

The length data are to be understood as approx. data. The abbreviations and designations used have the following meaning:
cat: chloramphenicol resistance gene
rep-ts: temperature-sensitive replication region of the plasmid pSC101
yjgF5': part of the 5' region of the yjgF ORF and the region lying upstream
yjgF3': part of the 3' region of the yjgF ORF and the region lying downstream The abbreviations for the restriction enzymes have the following meaning
EcoRV: restriction endonuclease from *Escherichia coli* RY13
Ec1136II: restriction endonuclease from *Escherichia coli*
HincII: restriction endonuclease from *Haemophilus influenzae* $R_c$
HindIII: restriction endonuclease from *Haemophilus influenzae* $R_D$
PstI: restriction endonuclease from *Providencia stuartii*
StuI: restriction endonuclease from *Streptomyces tubercidicus*
XbaI: Restriction endonuclease from *Xanthomonas badrii*

DETAILED DESCRIPTION OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Threonine is particularly preferred.

The term "attenuation" in this connection describes the reduction or elimination of the intracellular activity or concentration of one or more enzymes or proteins in a microorganism which are coded by the corresponding DNA, for example by using a weak promoter or a gene or allele or ORF, which codes for a corresponding enzyme or protein with a low activity or inactivates the corresponding enzyme or protein or gene or ORF and optionally combining these measures.

Open reading frame (ORF) describes a section of a nucleotide sequence which codes or can code for a protein or polypeptide or ribonucleic acid to which no function can be assigned according to the prior art. After assignment of a function to the nucleotide sequence section in question, it is in general referred to as a gene. Alleles are in general understood as meaning variants of a given gene. These are distinguished by differences in the nucleotide sequence.

The protein coded by a nucleotide sequence, i.e. an ORF, a gene or an allele, or the ribonucleic acid coded is in general called the gene product.

By attenuation measures, the activity or concentration of the corresponding protein according to the invention or also of proteins from the prior art is in general reduced to 0 to 75%, 0 to 50%, 0 to 25%, 0 to 10% or 0 to 5% of the, activity or concentration of the wild-type protein or of the activity or concentration of the protein in the starting microorganism.

The starting microorganism is understood as meaning the microorganism on which the inventive measures are carried out.

The process is characterized in that the following steps are carried out:
a) fermentation of microorganisms of the Enterobacteriaceae family which produce the desired L-amino acid and in which the yjgF ORF or nucleotide sequences which code for it is or are attenuated,
b) concentration of the corresponding L-amino acid in the medium or in the cells of the microorganisms of the Enterobacteriaceae family, and optionally
c) isolation of the desired L-amino acid, constituents of the fermentation broth and/or the biomass in its entirety or portions (>0 to 100%) thereof optionally remaining in the product.

The microorganisms, in particular recombinant microorganisms, which the present invention provides can produce L-amino acids from glucose, sucrose, lactose, fructose, maltose, molasses, optionally starch, optionally cellulose or from glycerol and ethanol. They are representatives of the Enterobacteriaceae family chosen from the genera Escherichia, Erwinia, Providencia and Serratia. The genera Escherichia and Serratia are preferred. Of the genus Escherichia in particular the species *Escherichia coli* and of the genus Serratia in particular the species *Serratia marcescens* are to be mentioned.

Suitable strains, which produce L-threonine in particular, of the genus Escherichia, in particular of the species *Escherichia coli*, are, for example

| | |
|---|---|
| *Escherichia coli* H4581 | (EP 0 301 572) |
| *Escherichia coli* KY10935 | (Bioscience |
| Biotechnology and Biochemistry 61(11): | 1877-1882 (1997) |
| *Escherichia coli* VNIIgenetika MG442 | (US-A-4278,765) |
| *Escherichia coli* VNIIgenetika M1 | (US-A-4.321.325) |
| *Escherichia coli* VNIIgenetika 472T23 | (US-A-5,631,157) |
| *Escherichia coli* BKIIM B-3996 | (US-A-5.175.107) |
| *Escherichia coli* kat 13 | (WO 98/04715) |
| *Escherichia coli* KCCM-10132 | (WO 00/09660) |

Suitable L-threonine-producing strains of the genus Serratia, in particular of the species *Serratia marcescens*, are, for example
Serratia marcescens HNr21 (Applied and Environmental Microbiology 38(6): 1045-1051 (1979))
Serratia marcescens TLr156 (Gene 57(2-3): 151-158 (1987))
Serratia marcescens T-2000 (Applied Biochemistry and Biotechnology 37(3): 255-265 (1992))

Strains from the Enterobacteriaceae family which produce L-threonine preferably have, inter alia, one or more genetic or phenotypic features chosen from the group consisting of: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to cyclopentane-carboxylic acid, resistance to rifampicin, resistance to valine analogues, such as, for example, valine hydroxamate, resistance to purine analogues, such as, for example, 6-dimethylaminopurine, a need for L-methionine, optionally a partial and compensatable need for L-isoleucine, a need for meso-diaminopimelic acid, auxotrophy in respect of threonine-containing dipeptides, resistance to L-threonine, resistance to threonine raffinate, resistance to L-homoserine, resistance to L-lysine, resistance to L-methionine, resistance to L-glutamic acid, resistance to L-aspartate, resistance-to L-leucine, resistance to L-phenylalanine, resistance to L-serine, resistance to L-cysteine, resistance to L-valine, sensitivity to fluoropyruvate, defective threonine dehydrogenase, optionally an ability for sucrose utilization, enhancement of the threonine operon, enhancement of homoserine dehydrogenase I-aspartate kinase I, preferably of the feed back resistant form, enhancement of homoserine kinase, enhancement of threonine synthase, enhancement of aspartate kinase, optionally of the feed back resistant form, enhancement of aspartate semialdehyde dehydrogenase, enhancement of phosphoenol pyruvate carboxylase, optionally of the feed back resistant form, enhancement of phosphoenol pyruvate synthase, enhancement of transhydrogenase, enhancement of the RhtB gene product, enhancement of the RhtC gene product, enhancement of the YfiK gene product, enhancement of a pyruvate carboxylase, and attenuation of acetic acid formation.

It has been found that microorganisms of the Enterobacteriaceae family produce L-amino acids, in particular L-threonine, in an improved manner after attenuation, in particular elimination, of the yjgF gene or open reading frame (ORF) or alleles thereof.

The nucleotide sequences of the genes or open reading frames (ORF) of *Escherichia coli* belong to the prior art and can also be found in the genome sequence of *Escherichia coli* published by Blattner et al. (Science 277: 1453-1462 (1997)).

The yjgF ORF of *Escherichia coli* K12 is described, inter alia, by the following data:
Description: open reading frame
Function: unknown function
Description: the open reading frame yjgF codes for a 15.1 kDa protein, the isoelectric point is 5.8; chromosomally located, for example in *E. coli* K12 MG1655 it lies in the intergene region of the genes mgtA, which codes for an Mg2+ transport ATPase of P-Typ1, and the pyrI gene, which codes for the regulatory subunit of aspartate carbamoyltransferase
Reference: Wasinger V C. and Humphery-Smith I.; FEMS Microbiology Letters 169(2): 375-382 (1998) Volz K.; Protein Science 8(11): 2428-2437 (1999)
Parsons et al.; Biochemistry 42(1): 80-89 (2003)
Accession No.: AE000495

The yjgF ORF from Salmonella typhimurium is described, inter alia, in the following reference: Enos-Berlage et al.; Journal of Bacteriology 180(24): 6519-6528 (1998)

The nucleic acid sequences can be found in the databanks of the National Center for Biotechnology Information (NCBI) of the National Library of Medicine (Bethesda, Md., USA), the nucleotide sequence databank of the European Molecular Biologies Laboratories (EMBL, Heidelberg, Germany or Cambridge, UK) or the DNA databank of Japan (DDBJ, Mishima, Japan).

For better clarity, the known sequence for the yjgF ORF of *Escherichia coli* is shown under SEQ ID No.1 and the sequence, which is also known, for the yjgF ORF of Salmonella typhimurium is shown under SEQ ID No. 11. The proteins coded by these reading frames are shown as SEQ ID No. 2 and SEQ ID No. 12.

The open reading frames described in the text references mentioned can be used according to the invention. Alleles of these open reading frames or genes, in particular from Enterobacteriaceae, which result from the degeneracy of the genetic code or due to mutations such as are described below can furthermore be used. The use of endogenous genes or open reading frames is preferred.

"Endogenous genes" or "endogenous nucleotide sequences" are understood as meaning the genes or open reading frames alleles or nucleotide sequences present in the population of a species.

Suitable alleles of the yjgF ORF include those which contain neutral-function mutations or "sense mutations". These include, inter alia, those which lead to at least one (1) conservative amino acid exchange in the protein coded by them. The maximum number of conservative amino acid exchanges can relate to 2, 3, 5, 10, 20 but in no case more than 30 amino acids. By the conservative amino acid exchanges mentioned, the functional capacity is lowered or increased by 0% to not more than 24%, 20%, 10%, 5%, 3%, 2% or 1%.

In the case of aromatic amino acids, conservative exchanges are referred to when phenylalanine, tryptophan and tyrosine are exchanged for one another. In the case of hydrophobic amino acids, conservative exchanges are referred to when leucine, isoleucine and valine are exchanged for one another. In the case of polar amino acids, conservative exchanges are referred to when glutamine and asparagine are exchanged for one another. In the case of basic amino acids, conservative exchanges are referred to when arginine, lysine and histidine are exchanged for one another. In the case of acidic amino acids, conservative exchanges are referred to when aspartic acid and glutamic acid are exchanged for one another. In the case of amino acids containing hydroxyl groups, conservative exchanges are referred to when serine and threonine are exchanged for one another. All other amino acid exchanges are called non-conservative amino acid exchanges.

In the same way, those nucleotide sequences which code for variants of the proteins mentioned which additionally contain a lengthening or shortening by at least one (1) amino acid on the N or C terminus can also be used. This lengthening or shortening is not more than 30, 20, 10, 5, 3 or 2 amino acids or amino acid radicals.

Suitable alleles also include those which code for proteins in which at least one (1) amino acid is inserted (insertion) or removed (deletion). The maximum number of such changes, called indels, can relate to 2, 3, 5, 10, 20 but in no case more than 30 amino acids.

Suitable alleles furthermore include those which are obtainable by hybridization, in particular under stringent conditions, using SEQ ID No. 1 or SEQ ID No. 11 or parts thereof, in particular the coding regions or the sequences complementary thereto.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is in general carried out under a relatively low stringency compared with the washing steps (Hybaid Hybridisation Guide, Hybaid Limited, Teddington, UK, 1996).

A buffer corresponding to 5×SSC buffer at a temperature of approx. 50° C.-68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50° C.-68° C. being established. It is optionally possible to lower the salt concentration to a concentration corresponding to 0.2×SSC or 0.1×SSC. Polynucleotide fragments which are, for example, at least 70% or at least 80% or at least 90% to 95% or at least 96% to 99% identical to the sequence of the probe employed can be isolated by increasing the hybridization temperature stepwise from 50° C. to 68° C. in steps of approx. 1-2° C. Further instructions on hybridization are obtainable on the market in the form of so-called kits (e.g. DIG Easy Hyb from Roche Diagnostics GmbH, Mannheim, Germany, Catalogue No. 1603558).

To achieve an attenuation, for example, expression of the genes or open reading frames or the catalytic properties of the enzyme proteins can be reduced or eliminated. The two measures can optionally be combined.

The reduction in gene expression can take place by suitable culturing, by genetic modification (mutation) of the signal structures of gene expression or also by the antisense-RNA technique. Signal structures of gene expression are, for example, repressor genes, activator genes, operators, promoters, attenuators, ribosome binding sites, the start codon and terminators. The expert can find information in this respect, inter alia, for example, in Jensen and Hammer (Biotechnology and Bioengineering 58: 191-195 (1998)), in Carrier und Keasling (Biotechnology Progress 15: 58-64 (1999)), Franch and Gerdes (Current Opinion in Microbiology 3: 159-164 (2000)) and in known textbooks of genetics and molecular biology, such as, for example, the textbook by Knippers ("Molekulare Genetik", 6th edition, Georg Thieme Verlag, Stuttgart, Germany, 1995) or that by Winnacker ("Gene und Klone", VCH Verlagsgesellschaft, Weinheim, Germany, 1990).

Mutations which lead to a change or reduction in the catalytic properties of enzyme proteins are known from the prior art. Examples which may be mentioned are the works of Qiu and Goodman (Journal of Biological Chemistry 272: 8611-8617 (1997)), Yano et al. (Proceedings of the National Academy of Sciences of the United States of America 95: 5511-5515 (1998)), Wente and Schachmann (journal of Biological Chemistry 266: 20833-20839 (1991)). Summarizing descriptions can be found in known textbooks of genetics and molecular biology, such as e.g. that by Hagemann ("Allgemeine Genetik", Gustav Fischer Verlag, Stuttgart, 1986).

Possible mutations are transitions, transversions, insertions and deletions of at least one (1) base pair or nucleotide. Depending on the effect of the amino acid exchange caused by the mutation on the enzyme activity, "missense mutations" or "nonsense mutations" are referred to. Missense mutation leads to an exchange of a given amino acid in a protein for another, this being, in particular, a non-conservative amino acid exchange. The functional capacity or activity of the protein is impaired by this means and reduced to a value of 0 to 75%, 0 to 50%, 0 to 25%, 0 to 10% or 0 to 5%. Nonsense mutation leads to a stop codon in the coding region of the gene and therefore to a premature interruption in the translation. Insertions or deletions of at least one base pair in a gene lead to "frame shift mutations", which lead to incorrect amino acids being incorporated or translation being interrupted prematurely. If a stop codon is formed in the coding region as a consequence of the mutation, this also leads to a premature termination of the translation. Deletions of at least one (1) or more codons typically also lead to a complete loss of the enzyme activity.

Instructions on generation of such mutations are prior art and can be found in known textbooks of genetics and molecular biology, such as e.g. the textbook by Knippers ("Molekulare Genetik", 6th edition, Georg Thieme Verlag, Stuttgart, Germany, 1995), that by Winnacker (",Gene und Klone", VCH Verlagsgesellschaft, Weinheim, Germany, 1990) or that by Hagemann ("Allgemeine Genetik", Gustav Fischer Verlag, Stuttgart, 1986).

Suitable mutations in the gene, such as-the deletion mutations mentioned by way of example (see SEQ ID No. 10), can be incorporated into suitable strains by gene or allele replacement.

A common method is the method, described by Hamilton et al. (Journal of Bacteriology 171: 4617-4622 (1989)), of gene replacement with the aid of a conditionally replicating pSC101 derivative pMAK705. Other methods described in the prior art, such as, for example, that of Martinez-Morales et al. (Journal of Bacteriology 181: 7143-7148 (1999)) or that of Boyd et al. (Journal of Bacteriology 182: 842-847 (2000)), can likewise be used.

It is also possible to transfer mutations in the particular genes or mutations which affect expression of the particular genes or open reading frames into various strains by conjugation or transduction.

More detailed explanations of the terms in genetics and molecular biology are found in known textbooks of genetics and molecular biology, such as, for example, the textbook by Birge (Bacterial and Bacteriophage Genetics, 4th ed., Springer Verlag, New York (USA), 2000) or the textbook by Berg, Tymoczko and Stryer (Biochemistry, 5th ed., Freeman and Company, New York (USA), 2002) or the handbook by Sambrook et al. (Molecular Cloning, A Laboratory Manual, (3 volume set), Cold Spring Harbor Laboratory Press, Cold Spring Harbor (USA), 2001).

It may furthermore be advantageous for the production of L-amino acids, in particular L-threonine, with strains of the Enterobacteriaceae family to enhance one or more enzymes of the known threonine biosynthesis pathway or enzymes of anaplerotic metabolism or enzymes for the production of reduced nicotinamide adenine dinucleotide phosphate or enzymes of glycolysis or PTS enzymes or enzymes of sulfur metabolism, in addition to the attenuation of the yjgF ORF.

The term "enhancement" in this connection describes the increase in the intracellular activity or concentration of one or more enzymes or proteins in a microorganism which are coded by the corresponding DNA, for example by increasing the number of copies of the gene or genes or open reading frames, using a potent promoter or a gene or open reading frame which codes for a corresponding enzyme or protein with a high activity, and optionally combining these measures.

By enhancement measures, in particular over-expression, the activity or concentration of the corresponding protein is in general increased by at least 10%, 25%, 50%, 75%, 100%,. 150%, 200%, 300%, 400% or 500%, up to a maximum of 1000% or 2000%, based on that of the wild-type protein or the activity or concentration of the protein in the starting microorganism.

For the production of L-amino acids, in particularly L-threonine, it may be advantageous, in addition to the attenuation of the yjgF ORF, at the same time for one or more of the genes chosen from the group consisting of the thrABC operon which codes for aspartate kinase, homoserine dehydrogenase, homoserine kinase and threonine synthase (U.S. Pat. No. 4,278,765), the pyc gene of Corynebacterium glutamicum which codes for pyruvate carboxylase (WO 99/18228), the pps gene which codes for phosphoenol pyruvate synthase (Molecular and General Genetics 231(2): 332-336 (1992)), the ppc gene which codes for phosphoenol pyruvate carboxylase (Gene 31: 279-283 (1984)), the pntA and pntB genes which code for transhydrogenase (European Journal of Biochemistry 158: 647-653 (1986)), the rhtB gene which imparts homoserine resistance (EP-A-0 994 190), the mqo gene which codes for malate:quinone oxidoreductase (WO 02/06459), the rhtC gene which imparts threonine resistance (EP-A-1 013 765), the thrE gene of Corynebacterium glutamicum which codes for the threonine export protein (WO 01/92545), the gdhA gene which codes for glutamate dehydrogenase (Nucleic Acids Research 11: 5257-5266 (1983); Gene 23: 199-209 (1983)), the hns gene which codes for the DNA-binding protein HLP-II (WO 03/004671), the pgm gene which codes for phosphoglucomutase (WO 03/004598), the fba gene which codes for fructose biphosphate aldolase (WO 03/004664), the ptsH gene of the ptsHIcrr operon which codes for the phosphohistidine protein hexose phosphotransferase of the phosphotransferase system PTS (WO 03/004674), the ptsI gene of the ptsHIcrr operon which codes for enzyme I of the phosphotransferase system PTS (WO 03/004674), the crr gene of the ptsHIcrr operon which codes for the glucose-specific IIA component of the phosphotransferase system PTS (WO 03/004674), the ptsG gene which codes for the glucose-specific IIBC component (WO 03/004670), the lrp gene which codes for the regulator of the leucine regulon (WO 03/004665), the csrA gene which codes for the global regulator Csr (Journal of Bacteriology 175: 4744-4755 (1993)), the fadR gene which codes for the regulator of the fad regulon (Nucleic Acids Research 16: 7995-8009 (1988)), the iclR gene which codes for the regulator of central intermediate metabolism (Journal of Bacteriology 172: 2642-2649 (1990)), the mopB gene which codes for the 10 kd chaperone (WO 03/004669) and is also known by the name groES, the ahpc gene of the ahpCF operon which codes for the small sub-unit of alkyl hydroperoxide reductase (WO 03/004663), the ahpF gene of the ahpCF operon which codes for the large sub-unit of alkyl hydroperoxide reductase (WO 03/004663), the cysK gene which codes for cysteine synthase A (WO 03/006666), the cysB gene which codes for the regulator of the cys regulon (WO 03/006666), the cysJ gene of the cysJIH operon which codes for the flavoprotein of NADPH sulfite reductase (WO 03/006666), the cysI gene of the cysJIH operon which codes for the haemoprotein-of NADPH sulfite reductase (WO 03/006666), the cysH gene of the cysJIH operon which codes for adenylyl sulfate reductase (WO 03/006666), the phoB gene of the phoBR operon which codes for the positive regulator PhoB of the pho regulon (WO 03/008606), the phoR gene of the phoBR operon which codes for the sensor protein of the pho regulon (WO 03/008606), the phoE gene which codes for protein E of-the outer cell membrane (WO 03/008606), the pykF gene which codes for fructose-stimulated pyruvate kinase I (WO 03/008609), the pfkB gene which codes for 6-phosphofructokinase II (WO 03/008610), the malE gene which codes for the periplasmic binding protein of maltose transport (WO 03/008605), the soda gene which codes for superoxide dismutase (WO 03/008613), the rseA gene of the rseABC operon which codes for a membrane protein with anti-sigmaE activity (WO 03/008612), the rseC gene of the rseABC operon which codes for a global regulator of the sigmaE factor (WO 03/008612), the sucA gene of the sucABCD operon which codes for the decarboxylase sub-unit of 2-ketoglutarate dehydrogenase (WO 03/008614), the sucB gene of the sucABCD operon which codes for the dihydrolipoyltranssuccinase E2 sub-unit of 2-ketoglutarate dehydrogenase (WO 03/008614), the sucC gene of the sucABCD operon which codes for the β-sub-unit of succinyl-CoA synthetase (WO 03/008615), the sucD gene of the sucABCD operon which codes for the α-sub-unit of succinyl-CoA synthetase (WO 03/008615), the adk gene which codes for adenylate kinase (Nucleic Acids Research 13(19): 7139-7151 (1985)), the hdeA gene which codes for a periplasmic protein with a chaperonin-like function (Journal of Bacteriology 175 (23): 7747-7748 (1993)), the hdeB gene which codes for a periplasmic protein with a chaperonin-like function (Journal of Bacteriology 175 (23): 7747-7748 (1993)), the icd gene which codes for isocitrate dehydrogenase (Journal of Biological Chemistry 262(22): 10422-10425 (1987)), the mglB gene which codes for the periplasmic, galactose-binding transport protein HLP-II (Molecular and General Genetics 229(3): 453-459 (19.91)), the lpd gene which codes for dihydrolipoamide dehydrogenase (European Journal of Biochemistry 135(3): 519-527 (1983)), the aceE gene which codes for the E1 component of the pyruvate dehydrogenase complex (European Journal of Biochemistry 133(1): 155-162 (1983)), the aceF gene which codes for the E2 component of the pyruvate dehydrogenase complex (European Journal of Biochemistry 133(3): 481-489 (1983)), the pepB gene which codes for aminopeptidase B (Journal of Fermentation and Bioengineering 82: 392-397 (1996)), the aldh gene which codes for aldehyde dehydrogenase (E.C. 1.2.1.3) (Gene 99(1): 15-23 (1991)), the bfr gene which codes for the iron storage homoprotein (bacterioferritin) (Journal of Bacteriology 171 (7): 3940-3947 (1989)), the udp gene which codes for uridine phosphorylase (Nucleic Acids Research 17(16): 6741 (1989)) and the rseB gene which codes the regulator of sigmaE factor activity (Molecular Microbiology 24(2): 355-371 (1997)), to be enhanced, in particular over-expressed.

The use of endogenous genes or open reading frames is in general preferred.

It may furthermore be advantageous for the production of L-amino acids, in particular threonine, in addition to the attenuation of the yjgF ORF, for one or more of the genes chosen from the group consisting of the tdh gene which codes for threonine dehydrogenase (Journal of Bacteriology 169: 4716-4721 (1987)), the mdh gene which codes for malate dehydrogenase (E.C. 1.1.1.37) (Archives in Microbiology 149: 3,6-42 (1987)), the gene product of the open reading frame (orf) yjfA (Accession Number AAC77180 of the National Center for Biotechnology Information (NCBI, Bethesda, Md., USA), WO 02/29080), the gene product of the open reading frame (orf) ytfP (Accession Number AAC77179 of the National Center for Biotechnology Information (NCBI, Bethesda, Md., USA), WO 02/29080), the pckA gene which codes for the enzyme phosphoenol pyruvate carboxykinase (WO 02/29080), the poxB gene which codes for pyruvate oxidase (WO 02/36797)

the aceA gene which codes for the enzyme isocitrate lyase (WO 02/081722), the dgsA gene which codes for the DgsA regulator of the phosphotransferase system (WO 02/081721) and is also known under the name of the mlc gene, the fruR gene which codes for the fructose repressor (WO 02/081698) and is also known under the name of the cra gene, the rpoS gene which codes for the sigma[38] factor (WO 01/05939) and is also known under the name of the katF gene, the aspA gene which codes for aspartate ammonium lyase (aspartase) (WO 03/008607) and the aceB gene which codes for malate synthase A (WO 03/008603)

to be attenuated, in particular eliminated or for the expression thereof to be reduced.

In addition to attenuation of the yjgF ORF it may furthermore be advantageous for the production of L-amino acids, in particular L-threonine, to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention can be cultured in the batch process (batch culture), the fed batch process (feed process) or the repeated fed batch process (repetitive feed process). A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and optionally cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

The fermentation is in general carried out at a pH of 5.5 to 9.0, in particular 6.0 to 8.0. Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 25° C. to 45° C., and preferably 30° C. to 40° C. Culturing is continued until a maximum of L-amino acids or L-threonine has formed. This target is usually reached within 10 hours to 160 hours.

The analysis of L-amino acids can be carried out by anion exchange chromatography with subsequent ninhydrin derivation, as described by Spackman et al. (Analytical Chemistry, 30: 1190-1206 (1958)) or it can be carried out by reversed phase HPLC, as described by Lindroth et al. (Analytical Chemistry 51: 1167-1174 (1979)).

The process according to the invention is used for the fermentative preparation of L-amino acids, such as, for example, L-threonine, L-isoleucine, L-valine, L-methionine, L-homoserine and L-lysine, in particular L-threonine.

A pure culture of the *Escherichia coli* K-12 strain DH5α/pMAK705 was deposited as DSM 13720 on 8th Sep. 2000 at the Deutsche Sammlung futr Mikroorganismen und Zellkulturen (DSMZ=German Collection of Microorganisms and Cell Cultures, Braunschweig, Germany) in accordance with the Budapest Treaty.

The present invention is explained in more detail in the following with the aid of embodiment examples.

The minimal (M9) and complete media (LB) for *Escherichia coli* used are described by J. H. Miller (A Short Course in Bacterial Genetics (1992), Cold Spring Harbor Laboratory Press). The isolation of plasmid DNA from *Escherichia coli* and all techniques of restriction, ligation, Klenow and alkaline phosphatase treatment are carried out by the method of Sambrook et al. (Molecular Cloning—A Laboratory Manual (1989) Cold Spring Harbor Laboratory Press). Unless described otherwise, the transformation of *Escherichia coli* is carried out by the method of Chung et al. (Proceedings of the National Academy of Sciences of the United States of America 86: 2172-2175 (1989)).

The incubation temperature for the preparation of strains and transformants is 37° C. Temperatures of 30° C. and 44° C. are used in the gene replacement method of Hamilton et al.

EXAMPLE 1

Construction of the Deletion Mutation of the yjgF ORF

Parts of the gene regions lying upstream and downstream of the yjgF ORF and parts of the 5' and 3' region of the yjgF ORF are amplified from *Escherichia coli* K12 using the polymerase chain reaction (PCR) and synthetic oligonucleotides. Starting from the nucleotide sequence of the yjgF ORF and sequences lying upstream and downstream in *E. coli* K12 MG1655 (SEQ ID No. 1, Accession Number AE000495), the following PCR primers are synthesized (MWG Biotech, Ebersberg, Germany):

```
yjgF-1:
5' - TCGCGATCTGGTACTGTAAG - 3'      (SEQ ID No. 3)

yjgF-2:
5' - CTGTACGTAAGGACCGATAG - 3'      (SEQ ID No. 4)

yjgF-3:
5' - CGCTGTTCGTCGCTAATCTT - 3'      (SEQ ID No. 5)

yjgF-4:
5' - GATCTTCTTCGGACCGATCA - 3'      (SEQ ID No. 6)
```

The chromosomal *E. coli* K12 MG1655 DNA employed for the PCR is isolated according to the manufacturer's instructions with "Qiagen Genomic-tips 100/G" (QIAGEN, Hilden, Germany). A DNA fragment approx. 622 bp in size from the 5' region of the yjgF ORF, called yjgF5' and shown in SEQ ID No. 7 and a DNA fragment approx. 612 bp in size from the 3' region of the yjgF ORF, called yjgF3' and shown in SEQ ID No. 8, can be amplified with the specific primers under standard PCR conditions (Innis et al. (1990) PCR Protocols. A Guide to Methods and Applications, Academic Press) with Taq-DNA polymerase (Gibco-BRL, Eggenstein, Germany).

The PCR products are each ligated with the vector pCR2.1TOPO (TOPO TA Cloning Kit, Invitrogen, Groningen, The Netherlands) in accordance with the manufacturers instructions and transformed into the *E. coli* strain TOP10F'. Selection of plasmid-carrying cells takes place on LB agar, to which 50 μg/ml ampicillin are added. After isolation of the plasmid DNA, the vector pCR2.1yjgF5' is cleaved with the restriction enzymes Ec1136II and XbaI and, after separation in 0.8% agarose gel, the yjgF5' fragment is isolated with the aid of the QIAquick Gel Extraction Kit (QIAGEN, Hilden, Germany). After isolation of the plasmid DNA the vector pCR2.1yjgF3' is cleaved with the enzymes EcoRV and XbaI and ligated with the yjgF5' fragment isolated. The *E. coli* strain DH5α is transformed with the ligation batch and plasmid-carrying cells are selected on LB agar, to which 50 μg/ml ampicillin are added. After isolation of the plasmid DNA those plasmids in which the mutagenic DNA sequence shown in SEQ ID No. 9 is cloned are detected by control cleavage with the enzymes HindIII/XbaI and StuI/HincII. One of the plasmids is called pCR2.1TOPOΔyjgF.

EXAMPLE 2

Construction of the Replacement Vector pMAK705ΔyjgF

Figure 1:
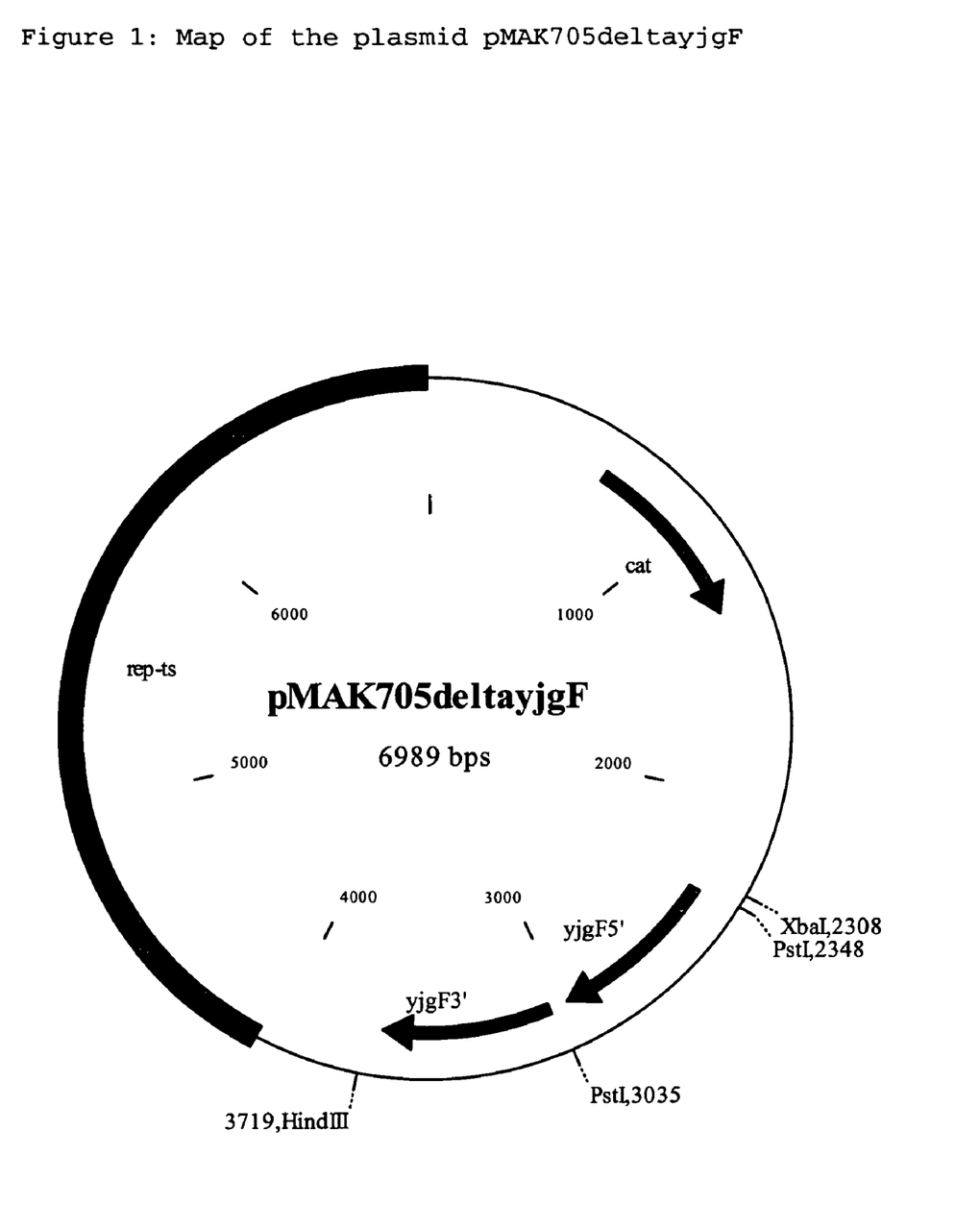
FIG. 1: pMAK705ΔyjgF (=pMAK705deltayjgF)

The deleted yjgF ORF described in example 1 is isolated from the vector pCR2.1TOPOΔyjgF after restriction with the enzymes HindIII and XbaI and separation in 0.8% agarose gel, and ligated with the plasmid pMAK705 (Hamilton et al. (1989) Journal of Bacteriology 171, 4617-4622), which had been digested with the enzymes HindIII and XbaI. The ligation batch is transformed in DH5α and plasmid-carrying cells are selected on LB agar, to which 20 μg/ml chloramphenicol are added. Successful cloning is demonstrated after isolation of the plasmid DNA and cleavage with the enzymes HindIII/XbaI and PstI. The replacement vector formed, pMAK705ΔyjgF (=pMAK705deltayjgF), is shown in FIG. 1.

EXAMPLE 3

Position-specific Mutagenesis of the yjgF ORF in the E. coli Strain MG442

The L-threonine-producing E. coli strain MG442 is described in the patent specification U.S. Pat. No. 4.278.765 and deposited as CMIM B-1628 at the Russian National Collection for Industrial Microorganisms (VKPM, Moscow, Russia).

For replacement of the chromosomal yjgF ORF with the plasmid-coded deletion construct, MG442 is transformed with the plasmid pMAK705ΔyjgF. The gene replacement is carried out by the selection method described by Hamilton et al. (1989) Journal of Bacteriology 171, 4617-4622) and is verified by standard PCR methods (Innis et al. (1990) PCR Protocols. A Guide to Methods and Applications, Academic Press) with the following oligonucleotide primers:

```
yjgF-1:
5' - TCGCGATCTGGTACTGTAAG - 3'    (SEQ ID No. 3)

yjgF-4:
5' - GATCTTCTTCGGACCGATCA - 3'    (SEQ ID No. 6)
```

After replacement has taken place, MG442 contains the form of the ΔyjgF allele shown in SEQ ID No. 10. The strain obtained is called MG442ΔyjgF.

EXAMPLE 4

Preparation of L-threonine with the Strain MG442ΔyjgF

MG442ΔyjgF is multiplied on minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar. The formation of L-threonine is checked in batch cultures of 10 ml contained in 100 ml conical flasks. For this, 10 ml of preculture medium of the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose are inoculated and the batch is incubated for 16 hours at 37° C. and 180 rpm on an ESR incubator from Kühner AG (Birsfelden, Switzerland). 250 μl of this preculture are transinoculated into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 30 g/l $CaCO_3$, 20 g/l glucose) and the batch is incubated for 48 hours at 37° C. After the incubation the optical density (OD) of the culture suspension is determined with an LP2W photometer from Dr. Lange (Düsseldorf, Germany) at a measurement wavelength of 660 nm.

The concentration of L-threonine formed is then determined in the sterile-filtered culture supernatant with an amino acid analyzer from Eppendorf-BioTronik (Hamburg, Germany) by ion exchange chromatography and post-column reaction with ninhydrin detection.

The result of the experiment is shown in Table 1.

TABLE 1

| Strain | OD (660 nm) | L-Threonine |
|---|---|---|
| MG442 | 6.0 | 1.5 |
| MG442ΔyjgF | 6.3 | 2.1 |

What is claimed is:

1. A process for producing L-threonine comprising:
    a) culturing or fermenting an *Escherichia coli* cell in a medium for a time and under conditions suitable for producing said L-threonine;
    b) isolating said L-threonine; and
    c) determining the amount of L-threonine isolated,
wherein the expression of the yjgF open reading frame of said *E. coli* cell is eliminated by one or more methods of mutagenesis selected from the group consisting of: deletion of all or at least one nucleotide of the yjgF open reading frame; insertion of at least one nucleotide in the yjgF open reading frame; and transitional or transversional mutagenesis with incorporation of a non-sense mutation in the yjgF open reading frame, wherein said elimination of the expression of the yjgF open reading frame results in an increased production of L-threonine by said *E. coli* cell relative to the amount of L-threonine produced in said *E. coli* cell prior to said elimination of the expression of the yjgF open reading frame; and wherein prior to elimination of the expression of the yjgF open reading frame, said yjgF open reading frame comprises the nucleotide sequence of SEQ ID NO: 1 and encodes the polypeptide of SEQ ID NO:2.

2. The process of claim 1, wherein the expression of the yjgF open reading frame has been eliminated by the deletion of at least one nucleotide of the yjgF open reading frame.

3. The process of claim 1, wherein said L-threonine is isolated from said *E. coli*.

4. The process of claim 1, wherein said L-threonine is isolated from said medium.

5. The process of claim 1, wherein culturing or fermenting is performed using a batch process.

6. The process of claim 1, wherein culturing or fermenting is performed using a fed batch process.

7. The process of claim 1, wherein culturing or fermenting is performed using a repeated fed batch process.

8. A process for producing L-threonine, comprising:
    a) culturing or fermenting an *Escherichia coli* cell in a medium for a time and under conditions suitable for producing said L-threonine; and
    b) recovering said L-threonine and determining the amount of said L-threonine recovered,
wherein the expression of the yjgF open reading frame of said *E. coli* has been eliminated by deletion of all of the yjgF open reading frame and wherein said yjgF open reading frame encodes the polypeptide of SEQ ID NO:2.

9. The process of claim 8, wherein said yjgF open reading frame has the nucleotide sequence of SEQ ID NO:1.

10. The process of claim 8, wherein constituents of the culture or fermentation broth and/or biomass in its entirety or portions thereof remain with the recovered L-threonine of step b).

11. The process of claim 8, wherein culturing or fermenting is performed using a batch process.

12. The process of claim 8, wherein culturing or fermenting is performed using a fed batch process.

13. The process of claim 8, wherein culturing or fermenting is performed using a repeated fed batch process.

* * * * *

UNITED STATES PATENT AND TRADEMARK OFFICE
CERTIFICATE OF CORRECTION

| | | |
|---|---|---|
| PATENT NO. | : 7,638,313 B2 | Page 1 of 1 |
| APPLICATION NO. | : 10/733776 | |
| DATED | : December 29, 2009 | |
| INVENTOR(S) | : Rieping | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 804 days.

Signed and Sealed this

Twenty-sixth Day of October, 2010

David J. Kappos
*Director of the United States Patent and Trademark Office*